United States Patent [19]
Sirrenberg et al.

[11] 4,103,022
[45] Jul. 25, 1978

[54] COMBATING ARTHROPODS WITH 3-(2,2,4,4-TETRAFLUORO-BENZ-1,3-DIOXIN-6-YL)-1-(SUBSTITUTED BENZOYL)-UREAS

[75] Inventors: Wilhelm Sirrenberg, Sprockhoevel; Hans-Ulrich Alles, Odenthal-Blecher; Ingeborg Hammann, Cologne; Wilhelm Stendel, Wuppertal, all of Fed. Rep. of Germany

[73] Assignee: Bayer Aktiengesellschaft, Leverkusen, Fed. Rep. of Germany

[21] Appl. No.: 821,445

[22] Filed: Aug. 3, 1977

[30] Foreign Application Priority Data

Aug. 24, 1976 [DE] Fed. Rep. of Germany ....... 2637947

[51] Int. Cl.² ...................... A01N 9/28; C07D 319/08
[52] U.S. Cl. ................................. 424/278; 260/340.3
[58] Field of Search ...................... 260/340.3; 424/278

[56] References Cited

U.S. PATENT DOCUMENTS 3,639,668   2/1972   Alles et al. ................ 260/340.3

*Primary Examiner*—Ethel G. Love
*Attorney, Agent, or Firm*—Burgess, Dinklage & Sprung

[57] ABSTRACT

Combating arthropods with 3-(2,2,4,4-tetrafluoro-benz-1,3-dioxin-6-yl)-1-(substituted-benzoyl)-ureas of the formula

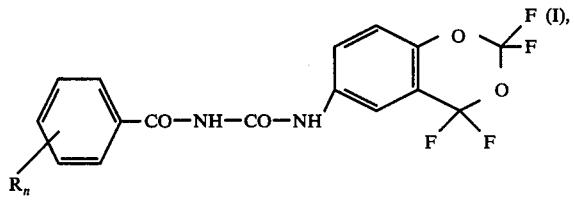

in which
R is halogen, alkyl or nitro, and
$n$ is 1, 2, 3, 4 or 5 which possess arthropodicidal properties.

10 Claims, No Drawings

COMBATING ARTHROPODS WITH 3-(2,2,4,4-TETRAFLUORO-BENZ-1,3-DIOXIN-6-YL)-1-(SUBSTITUTED BENZOYL)-UREAS

The present invention relates to and has for its objects the provision of particular new 3-(2,2,4,4-tetrafluorobenz-1,3-dioxin-6-yl)-1-(substituted-benzoyl)-ureas which possess arthropodicidal properties, active compositions in the form of mixtures of such compounds with solid and liquid dispersersible carrier vehicles, and methods for producing such compounds and for using such compounds in a new way especially for combating arthropods, e.g. insects, with other and further objects becoming apparent from a study of the within specification and accompanying examples.

It is known from German published Specification DOS No. 2,123,236 that certain benzoylureas, for example 1-(2,6-dichlorobenzoyl)-3-(4-chlorophenyl)-urea (compound A), possess insecticidal properties.

The present invention now provides, as new compounds, the substituted benzoylureas of the general formula

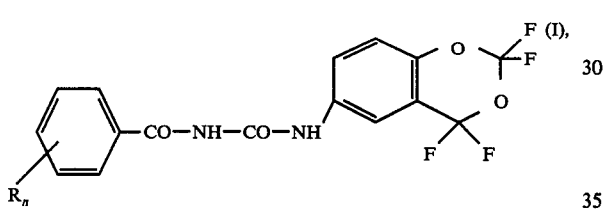

in which
R is halogen, alkyl or nitro, and
$n$ is 1, 2, 3, 4 or 5.

Preferably, R represents fluorine, chlorine, bromine, iodine, nitro or straight-chain or branched alkyl with 1 to 5, especially 1 or 2, carbon atoms, and $n$ represents 1, 2 or 3.

Surprisingly, the substituted benzoylureas according to the invention possess a substantially better insecticidal action than the closest 1-(2,6-dichlorobenzoyl)-3-(4-chlorophenyl)-urea of analogous structure and of the same type of action. The compounds according to the invention thus represent a genuine enrichment of the art.

The present invention also provides a process for the preparation of a substituted benzoylurea of the general formula (I) in which
(a) 6-amino-2,2,4,4-tetrafluoro-benz-1,3-dioxin, which has the formula

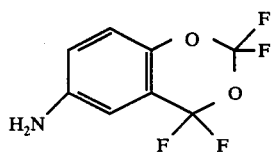

is reacted with a substituted benzoyl isocyanate of the general formula

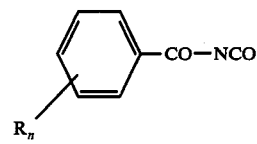

in which
R and $n$ have the above-mentioned meanings,
if appropriate in the presence of a diluent, or
(b) a substituted benzamide of the general formula

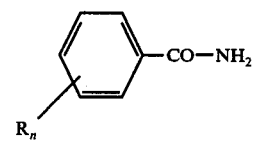

in which
R and $n$ have the above-mentioned meanings,
is reacted with 6-isocyanato-2,2,4,4-tetrafluoro-benz-1,3-dioxin, which has the formula

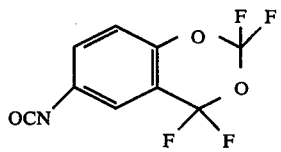

if appropriate in the presence of a diluent.

If, for example, 6-amino-2,2,4,4-tetrafluoro-benz-1,3-dioxin and 2-ethyl-benzoyl isocyanate are used as starting materials in process variant (a) or 6-isocyanato-2,2,4,4-tetrafluorobenz-1,3-dioxin and 2-fluoro-benzamide are used as starting materials in process variant (b), the course of the reactions can be represented by the following equations:

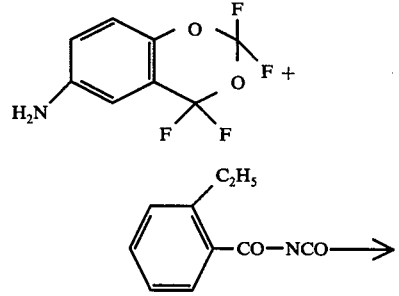

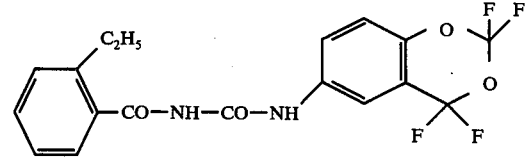

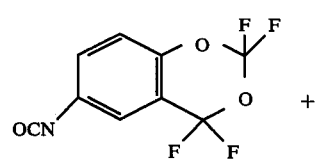

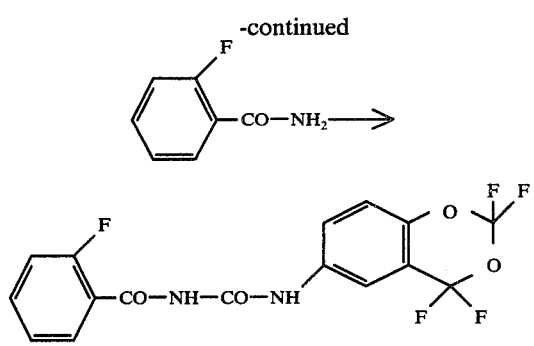

The benzoyl isocyanates (III) to be used as starting materials are known [see J. org. Chem. 30/12, page 4306– 4307 (1965)], as are the benzamides (IV) (see Beilstein "Handbuch der organischen Chemie" ("Handbook of Organic Chemistry"), volume 9, page 336). The following may be mentioned as individual examples: 2methyl-, 2-ethyl-, 4-methyl-, 4-ethyl-, 2-chloro-, 2-fluoro-, 2-bromo-, 2-iodo-, 2,6-dichloro-, 2,6-difluoro-, 2,6-dibromo-, 2,6-diiodo-, 2,3,6-trichloro-, 2,3,6-tribromo- and 2,3,6-triiodo-benzoyl isocyanate and -benzamide. 6-Amino-2,2,4,4-tetrafluoro-benz-1,3-dioxin (II) and 6-isocyanato-2,2,4,4-tetrafluoro-benz-1,3-dioxin (V), also to be used as starting materials, are known (from German Published Specifications DOS Nos. 1,643,382 and 1,768,244.

The process variants for the preparation of the substituted benzoylureas according to the invention are preferably carried out in the presence of a suitable solvent or diluent. Virtually all inert organic solvents can be used for this purpose, especially aliphatic and aromatic, optionally chlorinated hydrocarbons, such as benzene, xylene, toluene, chlorobenzene, benzine, methylene chloride, chloroform and carbon tetrachloride; ethers, for example diethyl ether, dibutyl ether and dioxane; ketones, for example acetone, methyl ethyl ketone, methyl isopropyl ketone and methyl isobutyl ketone; and nitriles, such as acetonitrile and propionitrile.

The reaction temperature in either process variant can be varied within a substantial range. In general, the reaction is carried out at from 0° to 120° C, preferably at from 50° to 80° C.

The reaction is in general allowed to take place under normal pressure.

To carry out the process, the starting components are in most cases employed in equimolar amounts. An excess of one or other reactant products no significant advantages. The reactants are in most cases brought together in one of the above-mentioned solvents and are, in most cases, stirred at an elevated temperature for one to several hours, to complete the reaction. After the mixture has cooled, the product which has precipitated is filtered off, washed, dried and, if appropriate, recrystallized. The compounds are in most cases obtained in a crystalline form and are characterized by their melting points.

The substituted benzoylureas according to the invention are not only active against plant pests but also, in the veterinary medicine field, against animal parasites (ectoparasites), such as parasitic fly larvae.

For this reason, the compounds according to the invention can be employed successfully as pesticides in plant protection and in the veterinary field.

The active compounds are well tolerated by plants, have a favorable level of toxicity to warm-blooded animals, and are suitable for combating arthropod pests, especially insects, which are encountered in agriculture, in forestry, in the protection of stored products and of materials, and in the hygiene field. They are active against normally sensitive and resistant species and against all or some stages of development. The above-mentioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and *Scutigera spec.;* from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus, Gryllotalpa spp., Locusta migratoria migratorioides, Melanoplus differentialis* and *Schistocerca gregaria;* from the order of the Dermaptera, for example *Forficula auricularia;* from the order of the Isoptera, for example *Reticulitermes spp.;* from the order of the Anoplura, for example *Phylloxera vastratrix, Pemphigus spp., Pediculus humanus corporis, Haematopinus spp.* and *Linognathus spp.;* from the order of the Mallophaga, for example *Trichodectes spp.* and *Damalinea spp.;* from the order of the Thysanoptera, for example *Hercinothrips femoralis* and *Thrips tabaci;* from the order of the Heteroptera, for example *Eurygaster spp., Dysdercus intermedius, Piesma quadrata, Cimex lectularius, Rhodnius prolixus* and *Triatoma spp.;* from the order of the Homoptera, for example *Aleurodes brassicae, Bemisia tabaci, Trialeurodes vaporariorum, Aphis gossypii, Brevicoryne brassicae, Cyrptomyzuz ribis, Doralis fabae, Doralis pomi, Eriosoma lanigerum, Hyalopterus arundinis, Macrosiphum avenae, Myzus spp., Phorodon humuli, Rhopalosiphum padi, Empoasca spp., Euscelis bilobatus, Nephotettix cincticeps, Lecanium corni, Saissetia oleae, Laodelphax striatellus, Nilaparvata Lugens, Aonidiella aurantii, Aspidiotus hederae, Pseudococcus spp.* and *psylla spp.;* from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria spp., Bucculatrix thurberiella, Phyllocnistis citrella, Agrotis spp., Euxoa spp., Feltia spp., Earias insulana, Heliothis spp., Laphygma exigua, Mamestra brassicae, Panolis flammea, Prodenia litura, Spodoptera spp., Trichoplusia ni, Carpocapsa pomonella, Pieris spp., Chilo spp., Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica spp., Psylliodes chrysocephala, Epilachna varivestis, Atomaria spp., Oryzaephilus surinamensis, Anthonomus spp., Sitophilus spp., Otiorrhynchus sulcatus, Cosmopolites sordidus, Ceuthorrhynchus assimilis, Hypera postica, Dermestes spp., Trogoderma spp., Anthrenus spp., Attagenus spp., Lyctus spp., Meligethes aeneus, Ptinus spp., Niptus hololeucus, Gibbium psylloides, Tribolium spp., Tenebrio molitor, Agriotes spp., Conoderus spp., Melolontha melolontha, Amphimallon solstitialis* and *Costelytra zealand-*

*ica;* from the order of the Hymenoptera, for example *Diprion spp., Hoplocampa spp., Lasius spp., Monomorium pharaonis* and *Vespa spp.;* from the order of the Diptera, for example *Aedes spp., Anopheles spp., Culex spp., Drosophila melanogaster, Musca spp., Fannia spp., Calliphora erythrocephala, Lucilia spp., Chyrsomyia spp., Cuterebra spp., Gastrophilus spp., Hyppobosca spp., Stomoxys spp., Oestrus spp., Hypoderma spp., Tabanus spp., Tannia spp., Bibio hortulanus, Oscinella frit, Phorbia spp., Pegomyia hyoscyami, Ceratitis capitata, Dacus oleae* and *Tipula paludosa;* from the order of the Siphonaptera, for example *Xenopsylla cheopis* and *Ceratophyllus spp.;* from the class of the Arachnida, for example *Scorpio maurus* and *Latrodectus mactans.*

When used against pests harmful to health and pests of stored products, the active compounds are distinguished by an excellent residual activity on wood and clay as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g., conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperature and pressures, such as halogenated hydrocarbons, e.g. dichlorodifluoromethane and trichlorofluoromethane, as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylene, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethylsulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as nonionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl or polyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other arthropodicides or nematocides, bactericides, fungicides, rodenticides, herbicides, fertilizers, growth-regulating agents, bird repellents, plant nutrients, agents for improving soil structure, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

In the veterinary field, the active compounds according to the invention may be used in a known manner, such as orally in the form of, for example, tablets, capsules, drenches and granules; dermally by means of, for example, dipping, spraying, pouring-on, spotting-on and powdering; and parenterally, for example by means of injections.

Furthermore, the present invention contemplates methods of selectively killing, combating or controlling pests, e.g. arthropods, especially insects and acarids, which comprises applying to at least one of correspondingly (a) such arthropods and (b) the corresponding habitat thereof, i.e. the locus to be protected, e.g. to a growing crop, to an area where a crop is to be grown or to a domestic animal, a correspondingly combative or toxic amount, i.e. an arthropodicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dry dressing, moist dressing, wet dressing, slurry dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Plutella test

Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dew moist and were then infested with caterpillars of the diamond-back moth (*Plutella maculipennis*).

After the specified periods of time, the degree of destruction was determined as a percentage: 100% meant that all the caterpillars were killed, whereas 0% meant that none of the caterpillars were killed.

The active compounds, the concentrations of the active compounds, the evaluation times and the results can be seen from the following table:

Table 1
(insects which damage plants)
*Plutella* test

| Active compounds | Active compound concentration in % | Degree of destruction in % after 7 days |
|---|---|---|
| 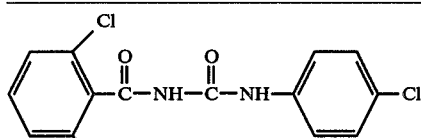 (known) (A) | 0.1<br>0.01 | 65<br>0 |
| 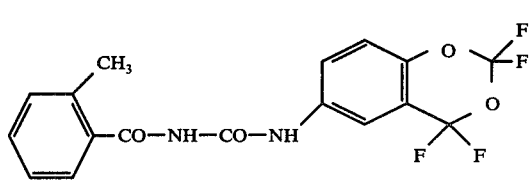 (8) | 0.1<br>0.01 | 100<br>100 |
| 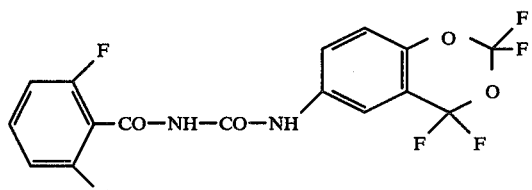 (1) | 0.1<br>0.01 | 100<br>100 |
| 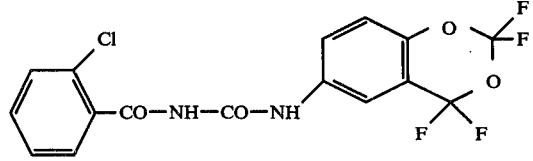 (5) | 0.1<br>0.01 | 100<br>100 |

Table 1-continued
(insects which damage plants)
*Plutella* test

| Active compounds | Active compound concentration in % | Degree of destruction in % after 7 days |
|---|---|---|
| 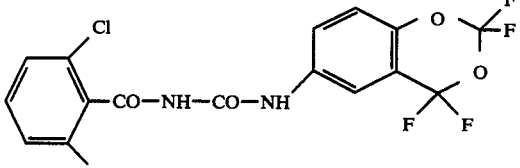 (6) | 0.1<br>0.01 | 100<br>100 |
| 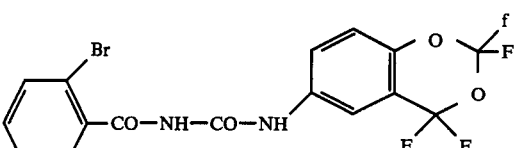 (3) | 0.1<br>0.01 | 100<br>100 |

EXAMPLE 2
Test with parasitic fly larvae

Solvent: 35 parts by weight of ethylene polyglycol monomethyl ether

Emulsifier: 35 parts by weight of nonylphenol polyglycol ether

To produce a suitable preparation of active compound, 30 parts by weight of the active substance in question were mixed with the stated amount of solvent which contained the above-mentioned proportion of emulsifier and the concentrate thus obtained was diluted with water to the desired concentration.

About 20 fly larvae (*Lucilia cuprina* resistant) were introduced into a test tube which contained approx. 2 cm³ of horse muscle. 0.5 ml of the preparation of active compound was applied to this horse meat. After 24 hours, the degree of destruction in % was determined. 100% meant that all the larvae had been killed and 0% meant that no larvae had been killed.

The active compounds, the concentrations of the active compounds and the results can be seen from the table which follows:

Table 2

| Active compound | Active compound concentration in ppm | Destructive action in % |
|---|---|---|
| 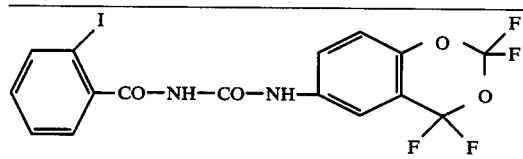 (4) | 1,000<br>300<br>100 | >50<br>>50<br>0 |
| 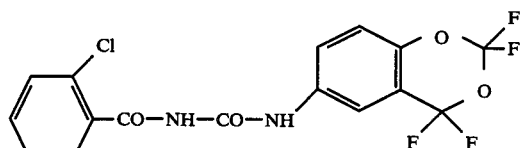 (5) | 1,000<br>300<br>100<br>30 | 100<br>100<br>100<br>0 |
| 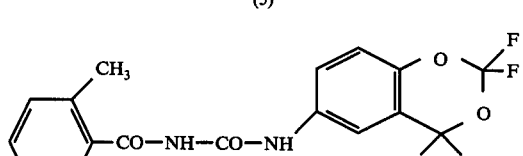 (8) | 1,000<br>300 | 100<br>0 |

The process of this invention is illustrated by the following preparative examples:

EXAMPLE 3

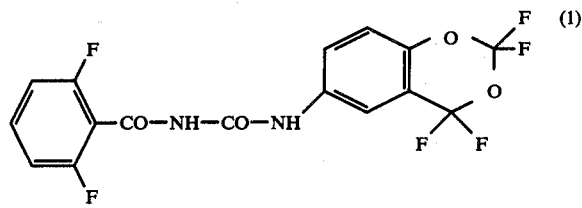

A solution of 5.5 g (0.03 mol) of 2,6-difluorobenzoyl isocyanate in 20 ml of toluene was added dropwise, at 60° C, to 6.7 g (0.03 mol) of 6-amino-2,2,4,4-tetrafluorobenz-1,3-dioxin in 100 ml of toluene. The batch was stirred for 1 hour at 60° C. After it had cooled, the product which had precipitated was filtered off, washed first with toluene and then with petroleum ether and then dried. 8 g (65.5% of theory) of analytically pure 3-(2,2,4,4-tetrafluoro-benz-1,3-dioxin-6-yl)-1-(2,6-difluorobenzoyl)-urea of melting point 231° C were obtained.

The following compounds were prepared analogously: Example 1.

Table 3

| Compound No. | Formula | Yield (% of theory) | Melting point ° C |
|---|---|---|---|
| (2) | *2-nitrophenyl-CO-NH-CO-NH-[3-(tetrafluorodioxin-6-yl)phenyl]* | 80 | 188 |
| (3) | *2-bromophenyl-CO-NH-CO-NH-[3-(tetrafluorodioxin-6-yl)phenyl]* | 59.5 | 172 |
| (4) | *2-iodophenyl-CO-NH-CO-NH-[3-(tetrafluorodioxin-6-yl)phenyl]* | 60.5 | 194 |
| (5) | *2-chlorophenyl-CO-NH-CO-NH-[3-(tetrafluorodioxin-6-yl)phenyl]* | — | — |
| (6) | *2,6-dichlorophenyl-CO-NH-CO-NH-[3-(tetrafluorodioxin-6-yl)phenyl]* | 38 | 206 |
| 7 | *2,3,6-trichlorophenyl-CO-NH-CO-NH-[3-(tetrafluorodioxin-6-yl)phenyl]* | 49 | 129 |
| 8 | *2-methylphenyl-CO-NH-CO-NH-[3-(tetrafluorodioxin-6-yl)phenyl]* | 52 | 184 |

Other compounds which can be similarly prepared include:

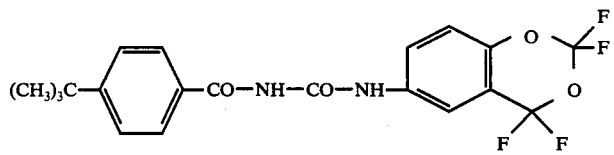

It will be appreciated that the instant specification and claims are set forth by way of illustration and not limitation, and that various modifications and changes may be made without departing from the spirit and scope of the present invention.

What is claimed is:

1. A 3-(2,2,4,4-tetrafluoro-benz-1,3-dioxin-6-yl)-1-benzoyl-urea of the formula

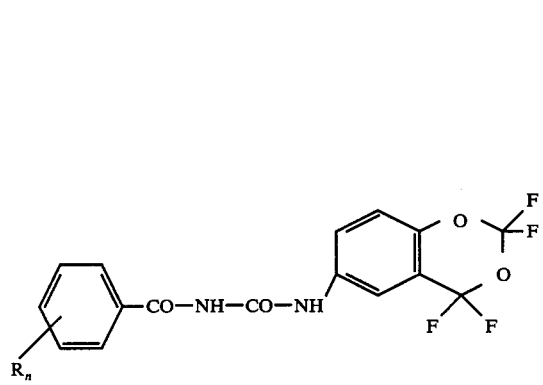

(I), in which
R is halogen, alkyl or nitro, and
n is 1, 2, 3, 4 or 5.

2. A compound according to claim 1, in which R is fluorine chlorine, bromine, iodine, nitro, or alkyl with 1 to 5 carbon atoms and n is 1, 2 or 3.

3. A compound according to claim 1, in which said compound is 3-(2,2,4,4-tetrafluoro-benz-1,3-dioxin-6-yl)-1-(2,6-difluorobenzoyl)-urea of the formula

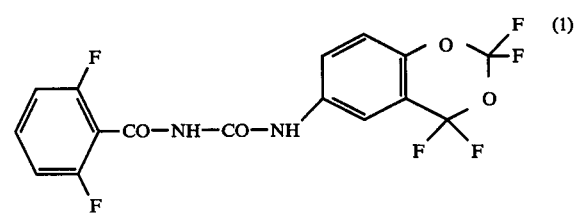

4. A compound according to claim 1, in which said compound is 3-(2,2,4,4-tetrafluoro-benz-1,3-dioxin-6-yl)-1-(2-bromobenzoyl)-urea of the formula

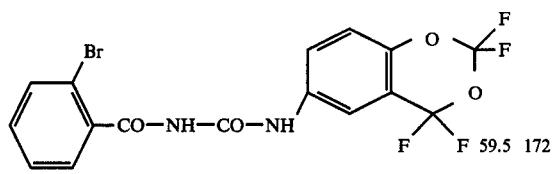

5. A compound according to claim 1, in which said compound is 3-(2,2,4,4-tetrafluoro-benz-1,3-dioxin-6-yl)-1-(2-chlorobenzoyl)-urea of the formula

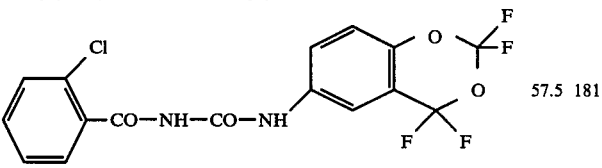

6. A compound according to claim 1, in which said compound is 3-(2,2,4,4-tetrafluoro-benz-1,3-dioxin-6-yl)-1-(2,6-dichlorobenzoyl)-urea of the formula

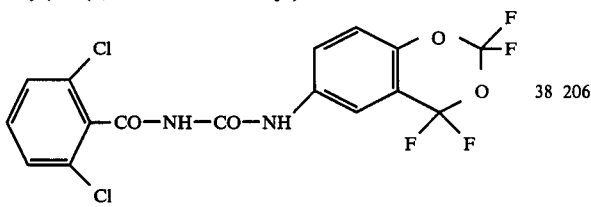

7. A compound according to claim 1, in which said compound is 3-(2,2,4,4-tetrafluoro-benz-1,3-dioxin-6-yl)-1-(2-methylbenzoyl)-urea of the formula

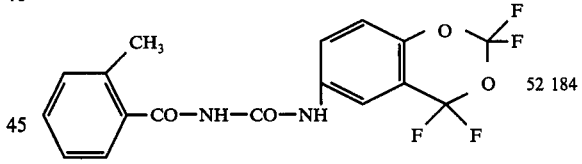

8. An anthropodicidal composition containing as active ingredient an arthropodicidally effective amount of a compound according to claim 1 in admixture with a diluent.

9. A method of combating arthropods which comprises applying to the arthropods, or to a habitat thereof, an arthropodicidally effective amount of a compound according to claim 1.

10. The method according to claim 9, in which said compound is 3-(2,2,4,4-tetrafluoro-benz-1,3-dioxin-6-yl)-1-(2,6-difluorobenzoyl)-urea,
3-(2,2,4,4-tetrafluoro-benz-1,3-dioxin-6-yl)-b 1-(2-bromobenzoyl)-urea,
3-(2,2,4,4-tetrafluoro-benz-1,3-dioxin-6-yl)-1-(2-chlorobenzoyl)-urea,
3-(2,2,4,4-tetrafluoro-benz-1,3-dioxin-6-yl)-1-(2,6-dichlorobenzoyl)-urea or
3-(2,2,4,4-tetrafluoro-benz-1,3-dioxin-6-yl)-1-(2-methyl-benzoyl)-urea.

* * * * *